United States Patent
Matsuo et al.

(10) Patent No.: US 11,911,545 B2
(45) Date of Patent: Feb. 27, 2024

(54) DIALYSIS BASE UNIT AND DIALYSIS SYSTEM

(71) Applicant: NIKKISO CO., LTD., Tokyo (JP)

(72) Inventors: Sumiaki Matsuo, Shizuoka (JP); Fumihiko Ishizaki, Shizuoka (JP); Hiroyuki Kawajiri, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 751 days.

(21) Appl. No.: 16/963,608

(22) PCT Filed: Oct. 26, 2018

(86) PCT No.: PCT/JP2018/039882
§ 371 (c)(1),
(2) Date: Jul. 21, 2020

(87) PCT Pub. No.: WO2019/146196
PCT Pub. Date: Aug. 1, 2019

(65) Prior Publication Data
US 2021/0060228 A1  Mar. 4, 2021

(30) Foreign Application Priority Data

Jan. 24, 2018 (JP) ................................. 2018-009754

(51) Int. Cl.
*A61M 1/16* (2006.01)
*B01D 61/32* (2006.01)

(52) U.S. Cl.
CPC ........ *A61M 1/1656* (2013.01); *A61M 1/1657* (2022.05); *B01D 61/32* (2013.01);
(Continued)

(58) Field of Classification Search
CPC ............ A61M 1/1656; A61M 2205/60; A61M 2205/3576; A61M 2205/583;
(Continued)

(56) References Cited

U.S. PATENT DOCUMENTS 8,400,298 B2   3/2013  Rada
9,511,182 B2  12/2016  Balschat et al.
(Continued)

FOREIGN PATENT DOCUMENTS

CA   2793109 A1   9/2011
CN  102791305 A  11/2012
(Continued)

OTHER PUBLICATIONS

Extended European Search Report dated Oct. 18, 2021 from related EP 18902926.7.
(Continued)

*Primary Examiner* — Joseph W Drodge
(74) *Attorney, Agent, or Firm* — Scully, Scott, Murphy & Presser, PC

(57) ABSTRACT

A dialysis base unit that is provided separately from a dialysate supply device for delivering dialysate and performs hemodialysis using the dialysate delivered from the dialysate supply device. The dialysis base unit includes a dialysate supply device identifying unit capable of identifying the dialysate supply device connected to the dialysis base unit. A dialysis system includes the dialysate supply device for delivering dialysate and the dialysis base unit.

5 Claims, 3 Drawing Sheets

(52) U.S. Cl.
CPC ............... *A61M 2205/3576* (2013.01); *A61M 2205/583* (2013.01); *A61M 2205/60* (2013.01)

(58) Field of Classification Search
CPC ........ A61M 2205/18; A61M 2205/276; A61M 2205/3561; A61M 2205/6018; A61M 1/14; A61M 1/16; A61M 1/1657; A61M 2205/6009; A61M 2205/6063; A61M 1/1654; A61M 2205/16; B01D 61/28; B01D 61/30; B01D 61/32
USPC .............................................. 210/646; 604/28
See application file for complete search history.

(56) References Cited

U.S. PATENT DOCUMENTS

| | | | | |
|---|---|---|---|---|
| 2009/0009290 | A1* | 1/2009 | Kneip | A61M 1/155 340/10.1 |
| 2010/0010426 | A1* | 1/2010 | Childers | A61M 1/155 604/29 |
| 2010/0315231 | A1 | 12/2010 | Rada | |
| 2011/0125085 | A1* | 5/2011 | McGill | A61M 1/1565 604/29 |
| 2012/0310148 | A1* | 12/2012 | Hedmann | A61M 1/28 604/28 |
| 2013/0001165 | A1 | 1/2013 | Pohlmeier et al. | |
| 2013/0062265 | A1 | 3/2013 | Balschat et al. | |
| 2013/0270160 | A1 | 10/2013 | Enjouji | |
| 2014/0018727 | A1* | 1/2014 | Burbank | A61M 1/1674 604/28 |
| 2014/0262990 | A1* | 9/2014 | Jones | A61M 1/1668 210/96.2 |
| 2014/0276375 | A1* | 9/2014 | Minkus | A61M 1/168 705/2 |
| 2015/0359954 | A1* | 12/2015 | Gerber | A61M 1/36 210/85 |
| 2018/0289879 | A1* | 10/2018 | Fulkerson | A61M 1/267 |

FOREIGN PATENT DOCUMENTS

| | | | |
|---|---|---|---|
| CN | 103037917 A | 4/2013 | |
| CN | 103372237 A | 10/2013 | |
| JP | 2006-271818 A | 10/2006 | |
| JP | 2010-000207 A | 1/2010 | |
| JP | 2012249751 A1 | 12/2012 | |
| JP | 2013-521906 A | 6/2013 | |
| JP | 2013-220191 A | 10/2013 | |
| JP | 5639200 B2 | 12/2014 | |
| JP | 2015123182 A | 7/2015 | |
| JP | 2016-147117 A | 8/2016 | |
| KR | 20130038803 A | 4/2013 | |
| WO | 102010011465 A1 | 9/2011 | |
| WO | WO 2011/13572 A1 | 9/2011 | |
| WO | WO 2015/174419 A1 | 11/2015 | |
| WO | WO2017035420 A1 * | 3/2017 | A61M 1/16 |

OTHER PUBLICATIONS

International Search Report dated Dec. 4, 2018 issued in PCT/JP2018/039882.
Translation of International Preliminary Report on Patentability and Written Opinion dated Aug. 6, 2020 issued in PCT/JP2018/039882.
Official Action dated Jul. 26, 2022 received from the China National Intellectual Property Administration in related application No. 201880087518.X together with English language translation.

* cited by examiner

DIALYSIS BASE UNIT AND DIALYSIS SYSTEM

TECHNICAL FIELD

The invention relates to a dialysis base unit and a dialysis system.

BACKGROUND ART

Various dialysate supply devices are used in dialysis systems for hemodialysis. For example, multi-patient dialysis fluid delivery devices used for CDDS (Central Dialysis fluid Delivery System) in hospitals, etc., devices having a function of preparing dialysate from undiluted dialysate fluid and water, and devices having a function of delivering dialysate from a bag, etc., and regenerating the used dialysate, etc., are known as the dialysate supply devices used for dialysis systems.

Dialysis systems using various dialysate supply devices have been conventionally developed and brought to the market, but these dialysis systems are manufactured respectively based on different concepts and it is necessary to use a dedicated dialysis system which is appropriate for a dialysate supply device to be used.

Patent Literature 1 discloses a dialysis system using dialysate and blood cartridges having a disposable flexible sheet unit. The dialysis system of Patent Literature 1 allows almost the same modules to support various dialysate supply devices. Hereinafter, a device, which is provided separately from the dialysate supply device and performs hemodialysis using the dialysate delivered from the dialysate supply device, is referred to as a dialysis base unit.

CITATION LIST

Patent Literature

Patent Literature 1: Japanese Patent No. 5639200

SUMMARY OF INVENTION

Technical Problem

In the meantime, in case that the dialysis base unit is configured to be connectable to various dialysate supply devices, it is sometimes necessary to take safety measures such as making suggestions to attach a deaerator unit when a dialysate supply device not having a deaeration function is connected. In addition, there are cases where conditions to be controlled on the dialysis base unit side are different depending on the dialysate supply device, and it is necessary to take appropriate measures in such a case.

Therefore, it is an object of the invention to provide a dialysis base unit and a dialysis system which can take appropriate measures according to a dialysate supply device to be used.

Solution to Problem

A dialysis base unit in an aspect of the invention is provided separately from a dialysate supply device for delivering dialysate and performs hemodialysis using the dialysate delivered from the dialysate supply device, the dialysis base unit comprising: a dialysate supply device identifying means capable of identifying the dialysate supply device connected to the dialysis base unit.

A dialysis system in an aspect of the invention is provided with a dialysate supply device for delivering dialysate, and the dialysis base unit.

Advantageous Effects of Invention

According to an aspect of the invention, it is possible to provide a dialysis base unit and a dialysis system which can take appropriate measures according to a dialysate supply device to be used.

DESCRIPTION OF EMBODIMENT

Embodiment

An embodiment of the invention will be described below in conjunction with the appended drawings.

Figure 1:
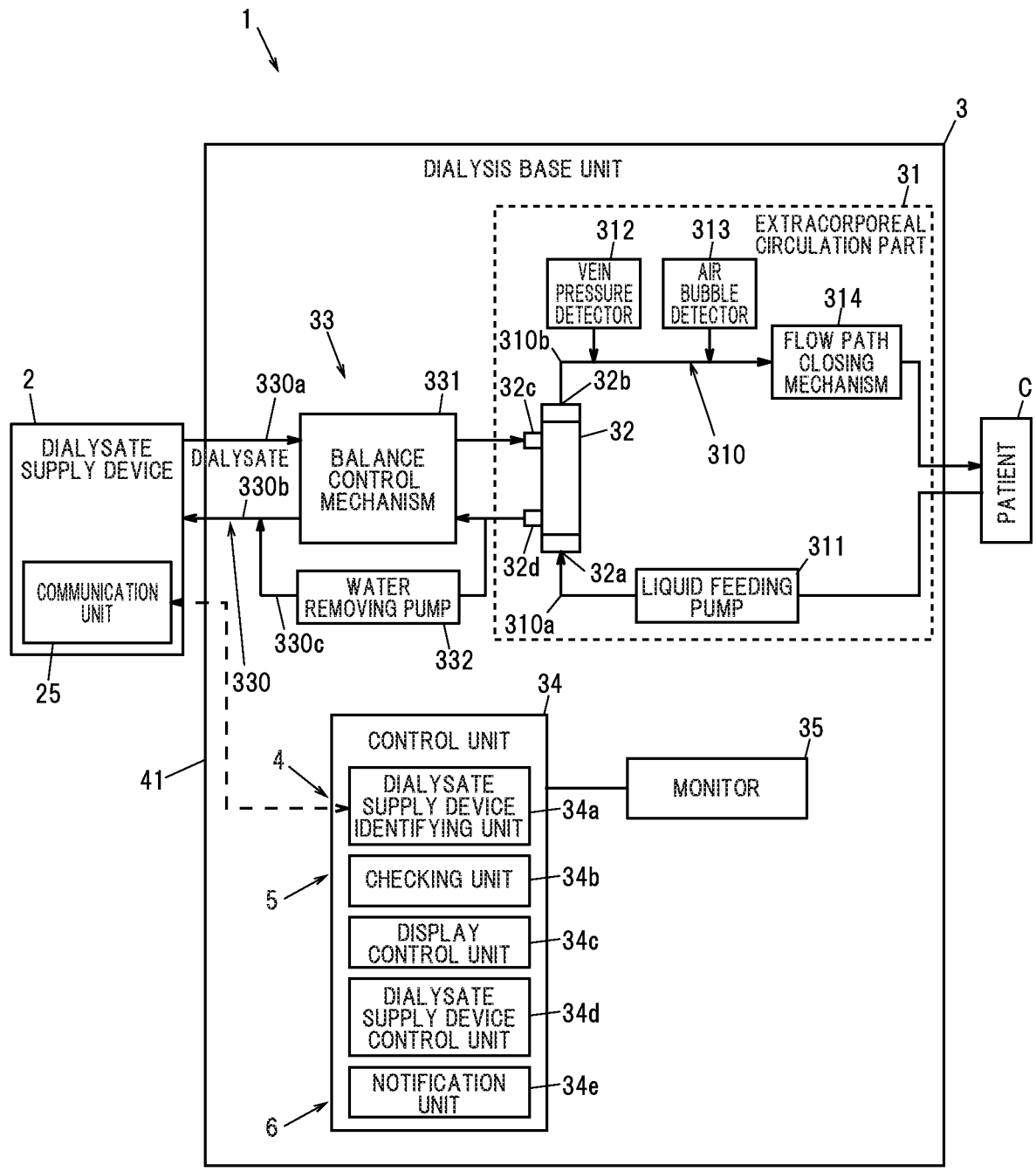
FIG. 1 is a schematic configuration diagram illustrating a dialysis system using a dialysis base unit in an embodiment of the present invention.

FIG. 1 is a schematic configuration diagram illustrating a dialysis system using a dialysis base unit in the present embodiment. A dialysis system 1 is provided with a dialysate supply device 2 for delivering dialysate, and a dialysis base unit 3 in the present embodiment.

Dialysate Supply Device 2

Figure 2A:
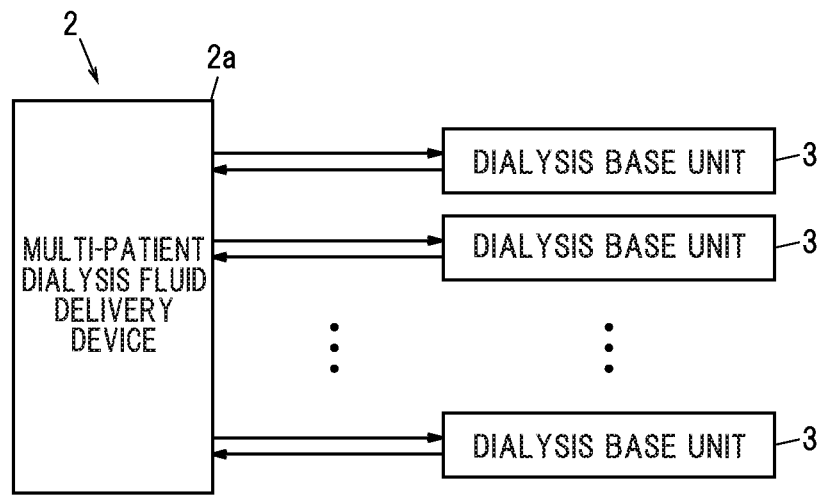
FIG. 2A is an explanatory diagram illustrating an example of a dialysate supply device.

The dialysate supply device 2 is a device for delivering dialysate to the dialysis base unit 3. For example, a multi-patient dialysis fluid delivery device 2a which delivers the dialysate to all of multiple dialysis base units 3 as shown in FIG. 2A is known as the dialysate supply device 2. The dialysate is delivered from the multi-patient dialysis fluid delivery device 2a to a device called monitoring device in a conventional dialysis system, but the dialysis base unit 3 serves as the monitoring device in the present embodiment.

Figure 2B:
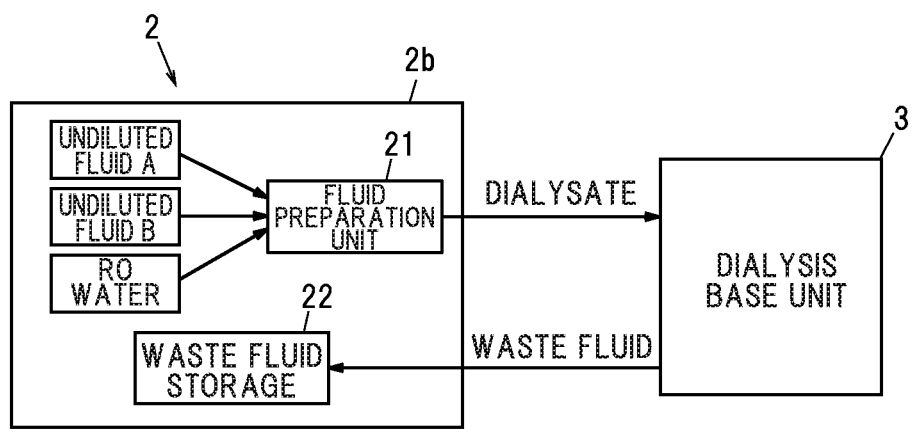
FIG. 2B is an explanatory diagram illustrating an example of the dialysate supply device.

As another dialysate supply device 2, there is a dialysate supply device 2b having a fluid preparation unit 21 for preparing dialysate from undiluted dialysate fluids (undiluted fluid A and undiluted fluid B shown in the drawing) and RO water, as shown in FIG. 2B. RO water is water obtained by removing impurities through a reverse osmosis membrane (RO: Reverse Osmosis). Although a system using two types of dialysate (the undiluted fluid A and the undiluted fluid B) is shown in FIG. 2B, it is not always necessary to use two types of undiluted fluids, and the dialysate may be prepared from, e.g., one undiluted fluid, or multiple undiluted fluids, and RO water. A combination of the dialysate supply device 2b having the fluid preparation unit 21 and the dialysis base unit 3 is sometimes called a personal dialysis machine. In other words, the dialysis base unit 3 can be used as a part of the personal dialysis machine. The dialysate supply device 2b is also provided with a waste fluid storage 22 which stores waste fluid discharged from the dialysis base unit 3. In this regard, however, the waste fluid may be directly drained from the dialysis base unit 3.

Figure 2C:
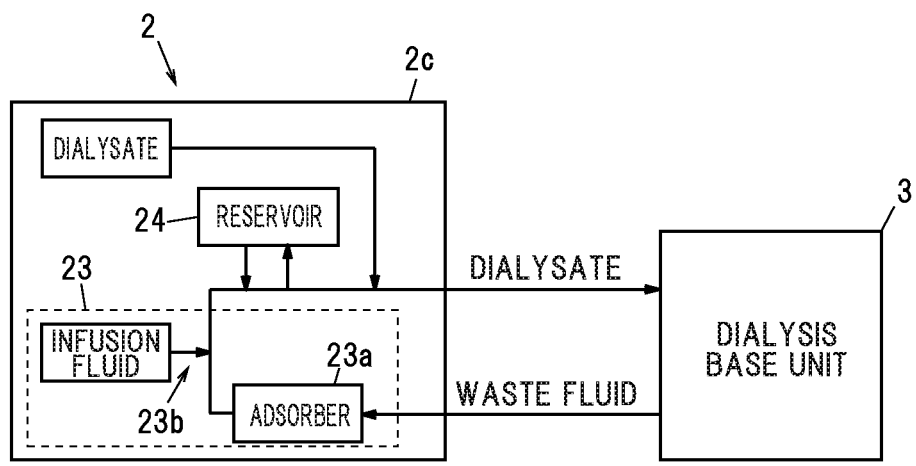
FIG. 2C is an explanatory diagram illustrating an example of the dialysate supply device.

As still another dialysate supply device 2, it is also possible to use a dialysate regeneration device 2c having a dialysate regeneration unit 23 which regenerates the used dialysate, as shown in FIG. 2C. Although the dialysate regeneration unit 23 in this example has an adsorber 23a adsorbing and removing ammonia and an infusion part 23b for infusing an infusion fluid used to adjust the components of the dialysate, the specific configuration of the dialysate regeneration unit 23 is not particularly limited. The dialysate regeneration device 2c also has a reservoir 24 for storing the dialysate. The dialysate used in the dialysate regeneration device 2c may be prepared by itself or may be supplied from another dialysate supply device (a dialysate preparation device).

Dialysis Base Unit 3

Back to FIG. 1, the dialysis base unit 3 performs hemodialysis using the dialysate delivered from the dialysate supply device 2. The dialysis base unit 3 is configured to be connectable to various types of the dialysate supply devices 2 as described in reference to FIGS. 2A to 2C.

The dialysis base unit 3 has an extracorporeal circulation part 31 having a blood circuit 310 capable of extracorporeally circulating blood of a patient C, a dialysis device 32 provided on the blood circuit 310, and a dialysate delivery and drainage part 33 having a dialysate circuit 330 through which the dialysate supplied from the dialysate supply device 2 is introduced into the dialysis device 32 and the dialysate discharged from the dialysis device 32 (waste fluid) is discharged to the outside of the dialysis base unit 3.

Dialysis Device 32

The dialysis device 32 is also called a dialyzer and has a blood purification membrane (a hollow-fiber hemodialysis filtration membrane, a flat hemodialysis membrane, or a hemofiltration membrane) thereinside. The dialysis device 32 has a blood inlet 32a for introducing blood and a blood outlet 32b for discharging the introduced blood, as well as a dialysate inlet 32c for introducing dialysate and a dialysate outlet 32d for discharging the introduced dialysate. In the dialysis device 32, blood is purified by bringing the blood into contact with the dialysate through the blood purification membrane.

Extracorporeal Circulation Part 31

The blood circuit 310 is formed of, e.g., a flexible tube, etc. The blood circuit 310 has an artery-side blood circuit 310a, through which the blood taken from a blood vessel of the patient C is guided to the blood inlet 32a of the dialysis device 32, and a vein-side blood circuit 310b, through which the blood discharged from the blood outlet 32b of the dialysis device 32 returns to the patient C. The extracorporeal circulation part 31 has a liquid feeding pump 311 which is placed on the artery-side blood circuit 310a and circulates the blood. The liquid feeding pump 311 is constructed from, e.g., a peristaltic pump which forces the blood to flow toward the dialysis device 32 by compressing a tube.

The extracorporeal circulation part 31 also has a vein pressure detector 312 which is placed on the vein-side blood circuit 310b to measure pressure of the blood flowing through the blood circuit 310, and an air bubble detector 313 which detects air bubbles in the blood. The air bubble detector 313 is configured to have, e.g., a pair of ultrasonic vibration elements (a means for generating oscillation and a means for receiving oscillation) formed of piezoelectric elements. A flow path closing mechanism 314 is also placed on the vein-side blood circuit 310b and closes the vein-side blood circuit 310b to stop the extracorporeal circulation of the blood when abnormality occurs, such as when air bubbles are detected by the air bubble detector 313. The vein pressure detector 312 and the air bubble detector 313 constitute the abnormality detecting means of the invention.

The extracorporeal circulation part 31 may additionally have, e.g., a mechanism for continuous infusion of anticoagulant (heparin, etc.) or a hematocrit sensor which measures a blood concentration (hematocrit level) and monitors progress of water removal, etc., even though it is not shown in the drawing.

Dialysate Delivery and Drainage Part 33

The dialysate circuit 330 is formed of, e.g., a flexible tube, etc. The dialysate circuit 330 has an introduction-side dialysate circuit 330a, through which the dialysate supplied form the dialysate supply device 2 is guided to the dialysate inlet 32c of the dialysis device 32, and a discharge-side dialysate circuit 330b, through which the dialysate discharged from the dialysate outlet 32d returns to the dialysate supply device 2.

The dialysate delivery and drainage part 33 has a balance control mechanism 331 which is placed over the introduction-side dialysate circuit 330a and the discharge-side dialysate circuit 330b and delivers the fluid so that the amount of the dialysate supplied to the dialysis device 32 is equal to the amount of the discharged fluid. The balance control mechanism 331 is constructed from, e.g., a dual pump which maintains equality between the supplied fluid and the discharged fluid by reciprocating movement of a plunger between two pump chambers with the same volume.

A bypass circuit 330c which bypasses the balance control mechanism 331 is provided on the discharge-side dialysate circuit 330b, and a water removing pump 332 is provided on the bypass circuit 330c. By running the water removing pump 332, the amount of the discharged fluid is increased to more than the amount of the dialysate supplied to the dialysis device 32 and water is removed from the blood.

Although it is not shown in the drawing, the dialysate delivery and drainage part 33 may additionally have an deaeration mechanism for removing oxygen dissolved in the dialysate, a filter for removing fine particles (endotoxin) from the dialysate, a blood leakage detector for detecting leakage of blood into the dialysate circuit 330, or a mechanism for calculating dialysis efficiency by exposing the dialysate after passing through the dialysis device 32 to ultraviolet light and measuring a solute concentration, etc.

Control Unit 34

The dialysis base unit 3 is provided with a control unit 34. The control unit 34 controls operation of the liquid feeding pump 311, the balance control mechanism 331 and the water removing pump 332. In addition, when it is determined, based on the detection result of the vein pressure detector 312 or the air bubble detector 313, that abnormality is occurring, the control unit 34 closes the blood circuit 310 by the flow path closing mechanism 314 and also emergently stops the liquid feeding pump 311, the balance control mechanism 331 and the water removing pump 332 from operating. The control unit 34 is realized by appropriately combining an arithmetic element such as CPU, a storage device such as memory, software and interface, etc.

In the present embodiment, the control unit 34 has a dialysate supply device identifying unit 34a, a checking unit 34b, a display control unit 34c, a dialysate supply device control unit 34d, and a notification unit 34e. Next, each unit will be described in detail.

Dialysate Supply Device Identifying Unit 34a

The dialysate supply device identifying unit 34a constitutes a dialysate supply device identifying means 4 of the invention and is provided to identify the dialysate supply device 2 connected to the dialysis base unit 3. In the present embodiment, the dialysate supply device identifying means 4 has the dialysate supply device identifying unit 34a and a signal line 41. The dialysate supply device identifying unit 34a is configured to identify the dialysate supply device 2 through wired communication with a communication unit 25 provided on the dialysate supply device 2, via the signal line 41. The signal line 41 constitutes a communication means for communication between the dialysis base unit 3 and the dialysate supply device 2. The signal line 41 may be a dedicated composite wire integrated with the dialysate circuit 330.

The dialysate supply device identifying unit 34a receives, e.g., a signal for identifying the dialysate supply device 2 (referred to as an identification signal) via the signal line 41 (the receiving means may be a request by the dialysate supply device identifying unit 34a or the identification signal may be sent from the communication unit). Based on the received identification signal, the dialysate supply device identifying unit 34a identifies the type (e.g., whether or not corresponding to any of the types shown in FIGS. 2A to 2C) or model of the dialysate supply device 2, in reference to a pre-stored database.

The dialysate supply device identifying unit 34a, when connected to, e.g., the dialysate supply device 2 not having a deaeration function, may be configured to encourage to take safety measures such as, e.g., displaying a suggestion of attaching a deaerator unit on a monitor 35 (to be described later) via the display control unit 34c.

Modification of Dialysate Supply Device Identifying Means 4

Although communication between the dialysate supply device identifying unit 34a and the communication unit 25 is performed by wired communication, it is not limited thereto and the dialysate supply device identifying unit 34a and the communication unit 25 may communicate wirelessly. The wireless communication method includes Bluetooth (registered trademark), etc. By providing wireless communication between the dialysate supply device identifying unit 34a and the communication unit 25, it is possible to easily identify the dialysate supply device 2 even when the dialysate supply device 2 is arranged at a position away from the dialysis base unit 3.

On the other hand, when the dialysate supply device 2 is arranged close to the dialysis base unit 3, the dialysate supply device identifying means 4 may be configured in such a manner that the identification signal is sent and received between the dialysate supply device identifying unit 34a and the communication unit 25 through near field communication using an IC tag, such as RFID (Radio Frequency IDentifier). In this case, an IC tag such as RF tag is mounted on the dialysate supply device 2, in placed of the communication unit 25.

Figure 3:
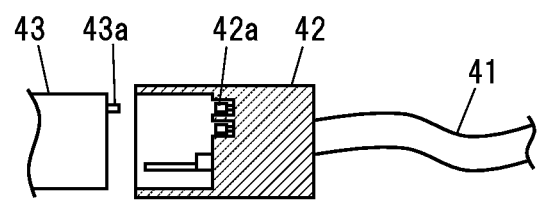
FIG. 3 is an explanatory diagram illustrating an example of a dialysate supply device identifying unit.

Alternatively, the dialysate supply device identifying means 4 may be configured in such a manner that, as shown in FIG. 3, plural switches 42a are formed on a connector 42 which connects the signal line 41 to the dialysate supply device 2, a protrusion 43a for pushing a specific switch 42a corresponding to the type or model of the dialysate supply device 2 is provided on a receptacle 43 formed on the dialysate supply device 2 and fitted into the connector 42, and the dialysate supply device 2 is identified by detecting which one of the switches 42a is pushed. The configuration shown in FIG. 3 is only an example and the shape, etc., of the switch 42a is not limited to that shown in the drawing.

Furthermore, the dialysate supply device identifying means 4 may be configured in such a manner that a pressure sensor for measuring the pressure of the dialysate or a concentration sensor for measuring the concentration of the dialysate is provided on the dialysate circuit 330, and the dialysate supply device identifying unit 34a detects whether or not the pressure or concentration is changed when a signal to change the discharge pressure or concentration of the dialysate is output to the dialysate supply device 2, thereby identifying the dialysate supply device 2.

The dialysate supply device identifying means 4 may also be configured that an input means is provided on the dialysis base unit 3 and the model or type of the dialysate supply device 2 is input by the input means. The input means may be, e.g., a manual entry-type input device configured in such a manner that, e.g., a model, etc., is selected from options of the models, etc., displayed on the monitor 35 (described later), or a button set for each model is pushed. When using a manual entry-type input device, sensors, etc., for identifying the dialysate supply device 2 are not required. Therefore, it is possible to simplify the system configuration of the dialysis system 1 and also to keep the cost down.

The input means is not limited to the manual entry-type, and may be a barcode reader which reads a model identification barcode attached to the dialysate supply device 2, or may be an image-capturing device such as camera. When an image-capturing device such as camera is used as the input means, the dialysate supply device identifying unit 34a is configured to determine the model, etc., of the dialysate supply device 2 based on the captured image (e.g., color or shape) of the dialysate supply device 2.

Checking Unit 34b

Back to FIG. 1, the checking unit 34b constitutes a checking means 5 and checks (i.e., verifies again) whether or not the dialysate supply device 2 identified by the dialysate supply device identifying means 4 is correct. As the checking means 5, it is possible to use the same means as the dialysate supply device identifying means 4 described above. That is, two means for identifying the dialysate supply device 2 are provided on the dialysis base unit 3, one used as the dialysate supply device identifying means 4 and the other as the checking means 5. Then, the checking unit 34b may be configured to use a different checking method depending on the identified dialysate supply device 2 in such a manner that, when the dialysate supply device identifying means 4 determines that, e.g., the dialysate supply device 2 capable of adjusting the dialysate concentration is connected, the checking unit 34b controls to make a change on the dialysate concentration adjustment and checks if the dialysate concentration is actually changed.

The checking unit 34b may be configured to perform an operation to ensure safety, such as displaying a warning on the monitor 35 via the display control unit 34c, when the dialysate supply device 2 identified by the dialysate supply device identifying means 4 is not correct. Providing the checking means 5 is not essential. However, it is desirable to provide the checking means since there is a possibility that the input is performed incorrectly especially when the manual entry-type input device is used as the dialysate supply device identifying means 4.

Display Control Unit 34c

In the present embodiment, the monitor 35 which displays the dialysis status or configurable conditions, etc., is provided on the dialysis base unit 3. The display control unit 34c changes the contents displayed on the monitor 35 to those appropriate for the dialysate supply device 2 identified by the dialysate supply device identifying means 4.

When the dialysate supply device 2 identified by the dialysate supply device identifying means 4 is, e.g., the multi-patient dialysis fluid delivery device 2a (see FIG. 2A), the display control unit 34c displays only the window of the temperature adjustment on the monitor 35. Meanwhile, when the dialysate supply device 2 identified by the dialysate supply device identifying means 4 is, e.g., the dialysate supply device 2b having the fluid preparation unit 21 (see FIG. 2B), the display control unit 34c displays the window of the dialysate concentration adjustment and the window of the remaining amount of the undiluted dialysate fluid (the undiluted fluid A and the undiluted fluid B) on the monitor 35, in addition to the window of the temperature adjustment. Furthermore, when the dialysate supply device 2 identified by the dialysate supply device identifying means 4 is, e.g., the dialysate regeneration device 2c (see FIG. 2C), the display control unit 34c displays the state of the dialysate stored in the reservoir 24 or the state of the adsorber 23a on the the monitor 35, in addition to the windows of the temperature adjustment and the dialysate concentration adjustment. These displayed contents are examples, and it is possible to appropriately set the contents to be displayed on the monitor 35.

Dialysate Supply Device Control Unit 34d

The dialysate supply device control unit 34d sends a control signal to the dialysate supply device 2 via the signal line 41 as the communication means and controls the dialysate supply device 2. The dialysate supply device control unit 34d is configured to change its control condition according to the dialysate supply device 2 identified by the dialysate supply device identifying means 4.

When the dialysate supply device 2 identified by the dialysate supply device identifying means 4 is, e.g., the multi-patient dialysis fluid delivery device 2a (see FIG. 2A), the dialysate supply device control unit 34d controls the multi-patient dialysis fluid delivery device 2a only within the controllable range (the dialysate temperature adjustment, etc.). Meanwhile, when the dialysate supply device 2 identified by the dialysate supply device identifying means 4 is, e.g., the dialysate supply device 2b having the fluid preparation unit 21 (see FIG. 2B), the dialysate supply device control unit 34d can control the dialysate temperature adjustment and the dialysate concentration adjustment, and also can perform control according to the remaining amount of the undiluted dialysate fluid. Furthermore, when the dialysate supply device 2 identified by the dialysate supply device identifying means 4 is, e.g., the dialysate regeneration device 2c (see FIG. 2C), the dialysate supply device control unit 34d controls the temperature adjustment, etc., within an appropriate control range according to the state of the adsorber 23a, the amount of the dialysate and the circulation flow rate. The control conditions of the dialysate supply device control unit 34d described here are only examples and can be appropriately set.

Notification Unit 34e

The notification unit 34e constitutes a notification means 6 of the invention, and sends a notification of detection of abnormality when abnormality is detected by the abnormality detecting means (the vein pressure detector 312 and the air bubble detector 313 in this example). In the present embodiment, the notification unit 34e is configured to be able to change a notification destination according to the dialysate supply device 2 identified by the dialysate supply device identifying means 4. The notification means 6 may have, e.g., an alarm device such as a light-emitting device or a buzzer attached to the dialysis base unit 3.

When the dialysate supply device 2 identified by the dialysate supply device identifying means 4 is, e.g., the multi-patient dialysis fluid delivery device 2a (see FIG. 2A), the notification unit 34e issues a notification in the dialysis base unit 3 as well as sends a notification to nurses' station or doctor's room since it is expected to be used in hospitals, etc. Meanwhile, when the dialysate supply device 2 identified by the dialysate supply device identifying means 4 is, e.g., the dialysate supply device 2b having the fluid preparation unit 21 (see FIG. 2B), the notification unit 34e issues a notification in the dialysis base unit 3 as well as sends a notification to a facility or a caregiver, etc., supporting the treatment of the patient C by emails, etc., since it is expected to be used at home. Examples of the notification in the dialysis base unit 3 includes display of a warning screen on the monitor 35 via the display control unit 34c, or a notification by light or sound using an alarm device such as a light-emitting device or a buzzer.

Functions and Effects of the Embodiment

As described above, the dialysis base unit 3 in the present embodiment is provided with the dialysate supply device identifying means 4 capable of identifying the connected dialysate supply device 2. As a result, it is possible to identify the dialysate supply device 2 to be used, and it is thus possible to take appropriate measures such as, e.g., changing the controlled conditions to those appropriate for the dialysate supply device 2 to be used, or changing the contents displayed on the monitor 35 to the appropriate display contents. Meanwhile, when some abnormality occurs, it is necessary to notify it to an appropriate notification destination according to a setting/place where the treatment is given. In this case, identifying the dialysate supply device 2 allows a setting/place using the dialysis base unit 3 to be determined and the notification of abnormality to be sent to the notification destination according the setting/place.

SUMMARY OF THE EMBODIMENT

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] dialysis base unit (3) that is provided separately from a dialysate supply device (2) for delivering dialysate and performs hemodialysis using the dialysate delivered from the dialysate supply device (2), the dialysis base unit (3) comprising: a dialysate supply device identifying means (4) capable of identifying the dialysate supply device (2) connected to the dialysis base unit (3).

[2] The dialysis base unit (3) described in [1], further comprising: a checking means (5) that checks whether or not the dialysate supply device (2) identified by the dialysate supply device identifying means (4) is correct.

[3] The dialysis base unit (3) described in [1] or [2], further comprising: a monitor (35) for displaying a dialysis status or configurable dialysis conditions; and a display control unit (34c) that changes contents displayed on the monitor (35) according to the dialysate supply device (2) identified by the dialysate supply device identifying means (4).

[4] The dialysis base unit (3) described in any one of [1] to [3], further comprising: a communication means for communicating with the dialysate supply device (2); and a dialysate supply device control unit (34d) that controls the dialysate supply device (2) via the communication means, wherein the dialysate supply device control unit (34d)

changes a control condition according to the dialysate supply device (2) identified by the dialysate supply device identifying means (4).

[5] The dialysis base unit (3) described in any one of [1] to [4], further comprising: an abnormality detecting means that detects abnormality during hemodialysis; and a notification means (6) that notifies detection of abnormality when abnormality is detected by the abnormality detecting means, wherein the notification means (6) is configured to be able to change a notification destination according to the dialysate supply device (2) identified by the dialysate supply device identifying means (4).

[6] A dialysis system (1), comprising: a dialysate supply device (2) for delivering dialysate;

and the dialysis base unit (3) described in any one of [1] to [5].

Although the embodiment of the invention has been described, the invention according to claims is not to be limited to the embodiment described above. Further, please note that all combinations of the features described in the embodiment are not necessary to solve the problem of the invention. In addition, the invention can be appropriately modified and implemented without departing from the gist thereof.

The invention claimed is:

1. A dialysis base unit comprising a dialyzer for performing hemodialysis using dialysate delivered from a dialysate supply device, the dialysis base unit further comprising:
a dialysate supply device identifying unit capable of identifying the dialysate supply device delivering dialysate to the dialysis base unit;
an abnormality detecting unit that detects an abnormality during the hemodialysis; and
a notification unit that notifies the detection of the abnormality detected by the abnormality detecting unit,
wherein the notification unit is configured to be able to change a notification destination according to the dialysate supply device identified by the dialysate supply device identifying unit, and
wherein the dialysate supply device identifying unit is configured to identify whether a type of the dialysate supply device delivering dialysate to the dialysis base unit is, one of, a dialysate supply device having a fluid preparation unit for preparing dialysate, a dialysate supply device having a multi-patient dialysis fluid delivery device which delivers the dialysate to all of multiple dialysis base units including the dialysis base unit, and a dialysate supply device having a dialysate regeneration unit which regenerates used dialysate.

2. The dialysis base unit according to claim 1, further comprising:
a checking unit that checks whether or not the dialysate supply device identified by the dialysate supply device identifying unit is correct.

3. The dialysis base unit according to claim 1, further comprising:
a monitor for displaying a dialysis status or for displaying configurable dialysis conditions; and
a display control unit that changes contents displayed on the monitor according to the dialysate supply device identified by the dialysate supply device identifying unit.

4. The dialysis base unit according to claim 1, further comprising:
a dialysate supply device control unit that controls the dialysate supply device,
wherein the dialysate supply device control unit changes a control condition according to the dialysate supply device identified by the dialysate supply device identifying unit.

5. A dialysis system, comprising:
a dialysate supply device for delivering dialysate, the dialysate supply device including a communication unit; and
a dialysis base unit comprising a dialyzer that is provided separately from the dialysate supply device for delivering dialysate and performs hemodialysis using the dialysate delivered from the dialysate supply device, the dialysis base unit further comprising:
a dialysate supply device identifying unit capable of identifying the dialysate supply device connected to the dialysis base unit;
an abnormality detecting unit that detects an abnormality during hemodialysis;
and a notification unit that notifies the detection of the abnormality detected by the abnormality detecting unit,
wherein the notification unit is configured to be able to change a notification destination according to the dialysate supply device identified by the dialysate supply device identifying unit, and
wherein the dialysate supply device identifying unit is configured to identify whether the type of the dialysate supply device connected to the dialysis base unit is, one of, a dialysate supply device having a fluid preparation unit for preparing dialysate, a dialysate supply device having a multi-patient dialysis fluid delivery device which delivers the dialysate to all of multiple dialysis base units including the dialysis base unit, or a dialysate supply device having a dialysate regeneration unit which regenerates used dialysate, based on a signal from the communication unit of the dialysate supply device.

* * * * *